(12) United States Patent
Banik et al.

(10) Patent No.: US 7,479,106 B2
(45) Date of Patent: Jan. 20, 2009

(54) AUTOMATED CONTROL OF IRRIGATION AND ASPIRATION IN A SINGLE-USE ENDOSCOPE

(75) Inventors: Michael S. Banik, Bolton, MA (US); Lucien Alfred Couvillon, Jr., Concord, MA (US); Anh Nguyen, Woburn, MA (US); William H. Stahley, Andover, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 392 days.

(21) Appl. No.: 10/955,901

(22) Filed: Sep. 30, 2004

(65) Prior Publication Data

US 2006/0069306 A1    Mar. 30, 2006

(51) Int. Cl.
    *A61B 1/12*  (2006.01)
(52) U.S. Cl. .................. 600/159; 600/118; 600/153; 600/156; 600/157; 600/158
(58) Field of Classification Search .......... 600/156–159
    See application file for complete search history.

(56) References Cited

U.S. PATENT DOCUMENTS

| 3,266,059 | A | 8/1966 | Stelle |
|---|---|---|---|
| 3,470,876 | A | 10/1969 | Barchilon |
| 3,572,325 | A | 3/1971 | Bazell et al. |
| 3,581,738 | A | 6/1971 | Moore |
| 4,108,211 | A | 8/1978 | Tanaka |
| 4,286,585 | A | 9/1981 | Ogawa |
| 4,294,162 | A | 10/1981 | Fowler et al. |
| 4,311,134 | A | 1/1982 | Mitsui et al. |
| 4,315,309 | A | 2/1982 | Coli |
| 4,351,323 | A | 9/1982 | Ouchi et al. |
| 4,425,113 | A | 1/1984 | Bilstad |
| 4,432,349 | A | 2/1984 | Oshiro |
| 4,471,766 | A | 9/1984 | Terayama |
| 4,473,841 | A | 9/1984 | Murakoshi et al. |
| 4,488,039 | A | 12/1984 | Sato et al. |
| 4,491,865 | A | 1/1985 | Danna et al. |
| 4,493,537 | A | 1/1985 | Nakahashi |
| 4,495,134 | A | 1/1985 | Ouchi et al. |

(Continued)

FOREIGN PATENT DOCUMENTS

DE      198 00 765 A1     4/1999

(Continued)

*Primary Examiner*—Linda C Dvorak
*Assistant Examiner*—Matthew J Kasztejna
(74) *Attorney, Agent, or Firm*—Christensen O'Connor Johnson Kindness PLLC

(57) ABSTRACT

The present invention is an integrated and automated irrigation and aspiration system for use in an endoscopic imaging system. The system provides for the automated cleaning of poorly prepared patients during a colonoscopy procedure as well as automated cleaning of an imaging system of an endoscope. The invention analyzes images obtained from an image sensor to detect the presence of an obstructed field of view, whereupon a wash routine is initiated to remove the obstruction. The wash routine may be adjusted in accordance with environmental conditions within the patient that are sensed by one or more sensors within the endoscope. In another embodiment, insufflation is automatically controlled to inflate a patient's colon as a function of one or more sensor readings obtained from one or more environmental sensor(s) on the endoscope.

13 Claims, 4 Drawing Sheets

U.S. PATENT DOCUMENTS

| | | | |
|---|---|---|---|
| 4,499,895 A | 2/1985 | Takayama | |
| 4,503,842 A | 3/1985 | Takayama | |
| 4,513,235 A | 4/1985 | Acklam et al. | |
| 4,515,444 A | 5/1985 | Prescott et al. | |
| 4,516,063 A | 5/1985 | Kaye et al. | |
| 4,519,391 A | 5/1985 | Murakoshi | |
| 4,552,130 A | 11/1985 | Kinoshita | |
| 4,559,928 A | 12/1985 | Takayama | |
| 4,566,437 A | 1/1986 | Yamaguchi | |
| 4,573,450 A | 3/1986 | Arakawa | |
| 4,580,210 A | 4/1986 | Nordstrom | |
| 4,586,923 A | 5/1986 | Gould et al. | |
| 4,615,330 A | 10/1986 | Nagasaki et al. | |
| 4,616,630 A | 10/1986 | Arakawa | |
| 4,617,915 A | 10/1986 | Arakawa | |
| 4,618,884 A | 10/1986 | Nagasaki | |
| 4,621,618 A | 11/1986 | Omagari | |
| 4,622,584 A | 11/1986 | Nagasaki et al. | |
| 4,625,714 A | 12/1986 | Toyota | |
| 4,631,582 A | 12/1986 | Nagasaki et al. | |
| 4,633,303 A | 12/1986 | Nagasaki et al. | |
| 4,633,304 A | 12/1986 | Nagasaki | |
| 4,643,170 A | 2/1987 | Miyazaki et al. | |
| 4,646,723 A | 3/1987 | Arakawa | |
| 4,649,904 A | 3/1987 | Krauter et al. | |
| 4,651,202 A | 3/1987 | Arakawa | |
| 4,652,093 A | 3/1987 | Stephen et al. | |
| 4,652,916 A | 3/1987 | Suzaki et al. | |
| 4,654,701 A | 3/1987 | Yabe | |
| RE32,421 E | 5/1987 | Hattori | |
| 4,662,725 A | 5/1987 | Nisioka | |
| 4,663,657 A | 5/1987 | Nagasaki et al. | |
| 4,667,655 A | 5/1987 | Ogiu et al. | |
| 4,674,844 A | 6/1987 | Nishioka et al. | |
| 4,686,963 A | 8/1987 | Cohen et al. | |
| 4,697,210 A | 9/1987 | Toyota et al. | |
| 4,700,693 A | 10/1987 | Lia et al. | |
| 4,714,075 A | 12/1987 | Krauter et al. | |
| 4,716,457 A | 12/1987 | Matsuo | |
| 4,719,508 A | 1/1988 | Sasaki et al. | |
| 4,727,417 A | 2/1988 | Kanno et al. | |
| 4,727,418 A | 2/1988 | Kato et al. | |
| 4,745,470 A | 5/1988 | Yabe et al. | |
| 4,745,471 A | 5/1988 | Takamura et al. | |
| 4,746,974 A | 5/1988 | Matsuo | |
| 4,748,970 A | 6/1988 | Nakajima | |
| 4,755,029 A | 7/1988 | Okobe | |
| 4,762,119 A | 8/1988 | Allred et al. | |
| 4,765,312 A | 8/1988 | Sasa et al. | |
| 4,766,489 A | 8/1988 | Kato | |
| 4,787,369 A | 11/1988 | Allred et al. | |
| 4,790,294 A | 12/1988 | Allred et al. | |
| 4,794,913 A | 1/1989 | Shimonaka et al. | |
| 4,796,607 A | 1/1989 | Allred et al. | |
| 4,800,869 A | 1/1989 | Nakajima | |
| 4,805,596 A | 2/1989 | Hatori | |
| 4,806,011 A | 2/1989 | Bettinger | |
| 4,819,065 A | 4/1989 | Eino | |
| 4,819,077 A | 4/1989 | Kikuchi et al. | |
| 4,821,116 A | 4/1989 | Nagasaki et al. | |
| 4,824,225 A | 4/1989 | Nishioka | |
| 4,831,437 A | 5/1989 | Nishioka et al. | |
| 4,836,187 A | 6/1989 | Iwakoshi et al. | |
| 4,844,052 A | 7/1989 | Iwakoshi et al. | |
| 4,844,071 A | 7/1989 | Chen et al. | |
| 4,845,553 A | 7/1989 | Konomura et al. | |
| 4,845,555 A | 7/1989 | Yabe et al. | |
| 4,847,694 A | 7/1989 | Nishihara | |
| 4,853,772 A | 8/1989 | Kikuchi | |
| 4,860,731 A | 8/1989 | Matsuura | |
| 4,867,546 A | 9/1989 | Nishioka et al. | |
| 4,868,647 A | 9/1989 | Uehara et al. | |
| 4,869,237 A | 9/1989 | Eino et al. | |
| 4,873,965 A | 10/1989 | Danieli | |
| 4,875,468 A | 10/1989 | Krauter et al. | |
| 4,877,314 A | 10/1989 | Kanamori | |
| 4,882,623 A | 11/1989 | Uchikubo | |
| 4,884,134 A | 11/1989 | Tsuji et al. | |
| 4,885,634 A | 12/1989 | Yabe | |
| 4,890,159 A | 12/1989 | Ogiu | |
| 4,894,715 A | 1/1990 | Uchikubo et al. | |
| 4,895,431 A | 1/1990 | Tsujiuchi et al. | |
| 4,897,789 A | 1/1990 | King et al. | |
| 4,899,731 A | 2/1990 | Takayama et al. | |
| 4,899,732 A | 2/1990 | Cohen | |
| 4,899,787 A | 2/1990 | Ouchi et al. | |
| 4,905,666 A | 3/1990 | Fukuda | |
| 4,916,533 A | 4/1990 | Gillies et al. | |
| 4,918,521 A | 4/1990 | Yabe et al. | |
| 4,919,112 A | 4/1990 | Siegmund | |
| 4,919,114 A | 4/1990 | Miyazaki | |
| 4,920,980 A | 5/1990 | Jackowski | |
| 4,928,172 A | 5/1990 | Uehara et al. | |
| 4,931,867 A | 6/1990 | Kikuchi | |
| 4,941,454 A | 7/1990 | Wood et al. | |
| 4,941,456 A | 7/1990 | Wood et al. | |
| 4,951,134 A | 8/1990 | Nakasima et al. | |
| 4,951,135 A | 8/1990 | Sasagawa et al. | |
| 4,952,040 A | 8/1990 | Igarashi | |
| 4,960,127 A | 10/1990 | Noce et al. | |
| 4,961,110 A | 10/1990 | Nakamura | |
| 4,967,269 A | 10/1990 | Sasagawa et al. | |
| 4,971,034 A * | 11/1990 | Doi et al. | 600/104 |
| 4,973,311 A | 11/1990 | Iwakoshi et al. | |
| 4,979,497 A | 12/1990 | Matsuura et al. | |
| 4,982,725 A | 1/1991 | Hibino et al. | |
| 4,984,878 A | 1/1991 | Miyano | |
| 4,986,642 A | 1/1991 | Yokota et al. | |
| 4,987,884 A | 1/1991 | Nishioka et al. | |
| 4,989,075 A | 1/1991 | Ito | |
| 4,989,581 A | 2/1991 | Tamburrino et al. | |
| 4,996,974 A | 3/1991 | Ciarlei | |
| 4,996,975 A | 3/1991 | Nakamura | |
| 5,001,556 A | 3/1991 | Nakamura et al. | |
| 5,005,558 A | 4/1991 | Aomori | |
| 5,005,957 A | 4/1991 | Kanamori et al. | |
| 5,007,408 A | 4/1991 | Ieoka | |
| 5,018,509 A | 5/1991 | Suzuki et al. | |
| 5,019,056 A | 5/1991 | Lee et al. | |
| 5,022,382 A | 6/1991 | Ohshoki et al. | |
| 5,029,016 A | 7/1991 | Hiyama et al. | |
| 5,034,888 A | 7/1991 | Uehara et al. | |
| 5,040,069 A | 8/1991 | Matsumoto et al. | |
| RE33,689 E | 9/1991 | Nishioka et al. | |
| 5,045,935 A | 9/1991 | Kikuchi | |
| 5,049,989 A | 9/1991 | Tsuji | |
| 5,050,584 A | 9/1991 | Matsuura | |
| 5,050,974 A | 9/1991 | Takasugi et al. | |
| 5,056,503 A | 10/1991 | Nagasaki | |
| 5,061,994 A | 10/1991 | Takahashi | |
| 5,068,719 A | 11/1991 | Tsuji | |
| 5,074,861 A | 12/1991 | Schneider et al. | |
| 5,081,524 A | 1/1992 | Tsuruoka et al. | |
| 5,087,989 A | 2/1992 | Igarashi | |
| 5,110,645 A | 5/1992 | Matsumoto et al. | |
| 5,111,281 A | 5/1992 | Sekiguchi | |
| 5,111,306 A | 5/1992 | Kanno et al. | |
| 5,111,804 A | 5/1992 | Funakoshi | |
| 5,113,254 A | 5/1992 | Kanno et al. | |
| 5,119,238 A | 6/1992 | Igarashi | |
| 5,131,393 A | 7/1992 | Ishiguro et al. | |
| 5,137,013 A | 8/1992 | Chiba et al. | |
| 5,140,265 A | 8/1992 | Sakiyama et al. | |
| 5,159,446 A | 10/1992 | Hibino et al. | |

| | | | | | |
|---|---|---|---|---|---|
| 5,170,774 A | 12/1992 | Heckele | 5,674,182 A | 10/1997 | Suzuki et al. |
| 5,170,775 A | 12/1992 | Tagami | 5,674,197 A | 10/1997 | van Muiden et al. |
| 5,172,225 A | 12/1992 | Takahashi et al. | 5,685,823 A | 11/1997 | Ito et al. |
| 5,174,293 A | 12/1992 | Hagiwara | 5,685,825 A | 11/1997 | Takase et al. |
| 5,176,629 A | 1/1993 | Kullas et al. | 5,691,853 A | 11/1997 | Miyano |
| 5,188,111 A | 2/1993 | Yates et al. | 5,695,450 A | 12/1997 | Yabe et al. |
| 5,191,878 A | 3/1993 | Iida et al. | 5,698,866 A | 12/1997 | Doiron et al. |
| 5,198,931 A | 3/1993 | Igarashi | 5,702,349 A | 12/1997 | Morizumi |
| 5,201,908 A | 4/1993 | Jones | 5,702,754 A | 12/1997 | Zhong |
| 5,208,702 A | 5/1993 | Shiraiwa | 5,703,724 A | 12/1997 | Miyano |
| 5,209,220 A | 5/1993 | Hiyama et al. | 5,704,371 A | 1/1998 | Shepard |
| 5,225,958 A | 7/1993 | Nakamura | 5,704,896 A | 1/1998 | Fukunishi et al. |
| 5,228,356 A | 7/1993 | Chuang | 5,708,482 A | 1/1998 | Takahashi et al. |
| 5,243,416 A | 9/1993 | Nakazawa | 5,721,566 A | 2/1998 | Rosenberg et al. |
| 5,243,967 A | 9/1993 | Hibino | 5,724,068 A | 3/1998 | Sanchez et al. |
| 5,257,628 A | 11/1993 | Ishiguro et al. | 5,728,045 A | 3/1998 | Komi |
| 5,271,381 A | 12/1993 | Ailinger et al. | 5,730,702 A | 3/1998 | Tanaka et al. |
| RE34,504 E | 1/1994 | Uehara et al. | 5,739,811 A | 4/1998 | Rosenberg et al. |
| 5,279,542 A | 1/1994 | Wilk | 5,740,801 A | 4/1998 | Branson |
| 5,291,010 A | 3/1994 | Tsuji | 5,746,696 A | 5/1998 | Kondo |
| 5,299,559 A | 4/1994 | Bruce et al. | 5,764,809 A | 6/1998 | Nomami et al. |
| 5,311,858 A | 5/1994 | Adair | 5,767,839 A | 6/1998 | Rosenberg |
| 5,325,845 A | 7/1994 | Adair et al. | 5,779,686 A | 7/1998 | Sato et al. |
| 5,331,551 A | 7/1994 | Tsuruoka et al. | 5,781,172 A | 7/1998 | Engel et al. |
| 5,342,299 A | 8/1994 | Snoke et al. | 5,788,714 A | 8/1998 | Ouchi |
| 5,347,987 A | 9/1994 | Feldstein et al. | 5,789,047 A | 8/1998 | Sasaki et al. |
| 5,347,989 A | 9/1994 | Monroe et al. | 5,793,539 A | 8/1998 | Konno et al. |
| 5,374,953 A | 12/1994 | Sasaki et al. | 5,805,140 A | 9/1998 | Rosenberg et al. |
| 5,379,757 A | 1/1995 | Hiyama et al. | 5,810,715 A | 9/1998 | Moriyama |
| 5,381,782 A | 1/1995 | DeLaRama et al. | 5,812,983 A | 9/1998 | Kumagai |
| 5,390,662 A | 2/1995 | Okada | 5,819,736 A | 10/1998 | Avny et al. |
| 5,400,769 A | 3/1995 | Tanii et al. | 5,820,591 A | 10/1998 | Thompson et al. |
| 5,402,768 A | 4/1995 | Adair | 5,821,466 A | 10/1998 | Clark et al. |
| 5,402,769 A | 4/1995 | Tsuji | 5,821,920 A | 10/1998 | Rosenberg et al. |
| 5,409,485 A | 4/1995 | Suda | 5,823,948 A | 10/1998 | Ross, Jr. et al. |
| 5,412,478 A | 5/1995 | Ishihara et al. | 5,827,176 A | 10/1998 | Tanaka et al. |
| 5,418,649 A | 5/1995 | Igarashi | 5,827,186 A | 10/1998 | Chen et al. |
| 5,420,644 A | 5/1995 | Watanabe | 5,827,190 A | 10/1998 | Palcic et al. |
| 5,429,596 A | 7/1995 | Arias et al. | 5,828,197 A | 10/1998 | Martin et al. |
| 5,431,645 A | 7/1995 | Smith et al. | 5,828,363 A | 10/1998 | Yaniger et al. |
| 5,434,615 A | 7/1995 | Matsumoto | 5,830,124 A | 11/1998 | Suzuki et al. |
| 5,436,640 A | 7/1995 | Reeves | 5,830,128 A | 11/1998 | Tanaka |
| 5,436,767 A | 7/1995 | Suzuki et al. | 5,836,869 A | 11/1998 | Kudo et al. |
| 5,440,341 A | 8/1995 | Suzuki et al. | 5,837,023 A | 11/1998 | Koike et al. |
| 5,464,007 A | 11/1995 | Krauter et al. | 5,840,014 A | 11/1998 | Miyano et al. |
| 5,469,840 A | 11/1995 | Tanii et al. | 5,841,126 A | 11/1998 | Fossum et al. |
| 5,473,235 A | 12/1995 | Lance et al. | 5,842,971 A | 12/1998 | Yoon |
| 5,482,029 A | 1/1996 | Sekiguchi et al. | 5,843,000 A | 12/1998 | Nishioka et al. |
| 5,484,407 A | 1/1996 | Osypka | 5,846,183 A | 12/1998 | Chilcoat |
| 5,485,316 A | 1/1996 | Mori et al. | 5,855,560 A | 1/1999 | Idaomi et al. |
| 5,492,131 A | 2/1996 | Galel | 5,857,963 A | 1/1999 | Pelchy et al. |
| 5,496,260 A | 3/1996 | Krauter et al. | 5,865,724 A | 2/1999 | Palmer et al. |
| 5,515,449 A | 5/1996 | Tsuruoka et al. | 5,868,664 A | 2/1999 | Speier et al. |
| 5,518,501 A | 5/1996 | Oneda et al. | 5,868,666 A | 2/1999 | Okada et al. |
| 5,518,502 A | 5/1996 | Kaplan et al. | 5,873,816 A | 2/1999 | Kagawa et al. |
| 5,543,831 A | 8/1996 | Tsuji et al. | 5,873,866 A | 2/1999 | Kondo et al. |
| 5,569,158 A | 10/1996 | Suzuki et al. | 5,876,326 A | 3/1999 | Takamura et al. |
| 5,569,159 A | 10/1996 | Anderson et al. | 5,876,331 A | 3/1999 | Wu et al. |
| 5,586,262 A | 12/1996 | Komatsu et al. | 5,876,373 A | 3/1999 | Giba et al. |
| 5,589,854 A | 12/1996 | Tsai | 5,876,427 A | 3/1999 | Chen et al. |
| 5,591,202 A | 1/1997 | Slater et al. | 5,877,819 A | 3/1999 | Branson |
| 5,608,451 A | 3/1997 | Konno et al. | 5,879,284 A | 3/1999 | Tsujita |
| 5,609,563 A * | 3/1997 | Suzuki et al. ............ 600/118 | 5,880,714 A | 3/1999 | Rosenberg et al. |
| 5,619,380 A | 4/1997 | Ogasawara et al. | 5,882,293 A | 3/1999 | Ouchi |
| 5,622,528 A | 4/1997 | Hamano et al. | 5,882,339 A | 3/1999 | Beiser et al. |
| 5,631,695 A | 5/1997 | Nakamura et al. | 5,889,670 A | 3/1999 | Schuler et al. |
| 5,633,203 A | 5/1997 | Adair | 5,889,672 A | 3/1999 | Schuler et al. |
| 5,643,203 A | 7/1997 | Beiser et al. | 5,892,630 A | 4/1999 | Broome |
| 5,643,302 A | 7/1997 | Beiser et al. | 5,895,350 A | 4/1999 | Hori |
| 5,645,075 A | 7/1997 | Palmer et al. | 5,897,507 A | 4/1999 | Kortenbach et al. |
| 5,647,840 A | 7/1997 | D'Amelio et al. | 5,897,525 A | 4/1999 | Dey et al. |
| 5,658,238 A | 8/1997 | Suzuki et al. | 5,907,487 A | 5/1999 | Rosenberg et al. |
| 5,667,477 A | 9/1997 | Segawa | 5,923,018 A | 7/1999 | Kameda et al. |

| | | | | | | |
|---|---|---|---|---|---|---|
| 5,928,136 | A | 7/1999 | Barry | 6,184,922 B1 | 2/2001 | Saito et al. |
| 5,929,607 | A | 7/1999 | Rosenberg et al. | 6,193,714 B1 | 2/2001 | McGaffigan et al. |
| 5,929,846 | A | 7/1999 | Rosenberg et al. | 6,195,592 B1 | 2/2001 | Schuler et al. |
| 5,929,900 | A | 7/1999 | Yamanaka | 6,203,493 B1 | 3/2001 | Ben-Haim |
| 5,929,901 | A | 7/1999 | Adair et al. | 6,206,824 B1 | 3/2001 | Ohara et al. |
| 5,931,833 | A | 8/1999 | Silverstein | 6,211,904 B1 | 4/2001 | Adair |
| 5,933,809 | A | 8/1999 | Hunt et al. | 6,216,104 B1 | 4/2001 | Moshfeghi et al. |
| 5,935,085 | A | 8/1999 | Welsh et al. | 6,219,091 B1 | 4/2001 | Yamanaka et al. |
| 5,936,778 | A | 8/1999 | Miyano et al. | 6,221,070 B1 | 4/2001 | Tu et al. |
| 5,941,817 | A | 8/1999 | Crawford | 6,238,799 B1 | 5/2001 | Opolski |
| 5,950,168 | A | 9/1999 | Simborg et al. | 6,241,668 B1 | 6/2001 | Herzog |
| 5,951,462 | A | 9/1999 | Yamanaka | 6,260,994 B1 | 7/2001 | Matsumoto et al. |
| 5,956,416 | A | 9/1999 | Tsuruoka et al. | 6,261,226 B1 | 7/2001 | McKenna et al. |
| 5,956,689 | A | 9/1999 | Everhart | 6,272,470 B1 | 8/2001 | Teshima |
| 5,956,690 | A | 9/1999 | Haggerson et al. | 6,275,255 B1 | 8/2001 | Adair et al. |
| 5,959,613 | A | 9/1999 | Rosenberg et al. | 6,282,442 B1 | 8/2001 | DeStefano et al. |
| 5,976,070 | A | 11/1999 | Ono et al. | 6,283,960 B1 | 9/2001 | Ashley |
| 5,976,074 | A | 11/1999 | Moriyama | 6,295,082 B1 | 9/2001 | Dowdy et al. |
| 5,980,454 | A | 11/1999 | Broome | 6,299,625 B1 | 10/2001 | Bacher |
| 5,980,468 | A | 11/1999 | Zimmon | 6,309,347 B1 | 10/2001 | Takahashi et al. |
| 5,986,693 | A | 11/1999 | Adair et al. | 6,310,642 B1 | 10/2001 | Adair et al. |
| 5,991,729 | A | 11/1999 | Barry et al. | 6,319,196 B1 | 11/2001 | Minami |
| 5,991,730 | A | 11/1999 | Lubin et al. | 6,319,197 B1 | 11/2001 | Tsuji et al. |
| 5,999,168 | A | 12/1999 | Rosenberg et al. | 6,334,844 B1 | 1/2002 | Akiba |
| 6,002,425 | A | 12/1999 | Yamanaka et al. | 6,346,075 B1 | 2/2002 | Arai et al. |
| 6,007,482 | A | 12/1999 | Madni et al. | 6,354,992 B1 * | 3/2002 | Kato .......................... 600/157 |
| 6,007,531 | A | 12/1999 | Snoke et al. | 6,366,799 B1 | 4/2002 | Acker et al. |
| 6,014,630 | A | 1/2000 | Jeacock et al. | 6,381,029 B1 | 4/2002 | Tipirneni |
| 6,015,088 | A | 1/2000 | Parker et al. | 6,398,724 B1 | 6/2002 | May et al. |
| 6,017,322 | A | 1/2000 | Snoke et al. | 6,413,207 B1 | 7/2002 | Minami |
| 6,020,875 | A | 2/2000 | Moore et al. | 6,421,078 B1 | 7/2002 | Akai et al. |
| 6,020,876 | A | 2/2000 | Rosenberg et al. | 6,425,535 B1 | 7/2002 | Akiba |
| 6,026,363 | A | 2/2000 | Shepard | 6,425,858 B1 | 7/2002 | Minami |
| 6,030,360 | A | 2/2000 | Biggs | 6,436,032 B1 | 8/2002 | Eto et al. |
| 6,032,120 | A | 2/2000 | Rock et al. | 6,441,845 B1 | 8/2002 | Matsumoto |
| 6,039,728 | A | 3/2000 | Berlien et al. | 6,447,444 B1 | 9/2002 | Avni et al. |
| 6,043,839 | A | 3/2000 | Adair et al. | 6,449,006 B1 | 9/2002 | Shipp |
| 6,050,718 | A | 4/2000 | Schena et al. | 6,453,190 B1 | 9/2002 | Acker et al. |
| 6,057,828 | A | 5/2000 | Rosenberg et al. | 6,454,162 B1 | 9/2002 | Teller |
| 6,059,719 | A | 5/2000 | Yamamoto et al. | 6,459,447 B1 | 10/2002 | Okada et al. |
| 6,061,004 | A | 5/2000 | Rosenberg | 6,468,204 B2 | 10/2002 | Sendai et al. |
| 6,066,090 | A | 5/2000 | Yoon | 6,475,141 B2 | 11/2002 | Abe |
| 6,067,077 | A | 5/2000 | Martin et al. | 6,478,730 B1 | 11/2002 | Bala et al. |
| 6,071,248 | A | 6/2000 | Zimmon | 6,489,987 B1 | 12/2002 | Higuchi et al. |
| 6,075,555 | A | 6/2000 | Street | 6,496,827 B2 | 12/2002 | Kozam et al. |
| 6,078,308 | A | 6/2000 | Rosenberg et al. | 6,498,948 B1 | 12/2002 | Ozawa et al. |
| 6,078,353 | A | 6/2000 | Yamanaka et al. | 6,503,193 B1 | 1/2003 | Iwasaki et al. |
| 6,078,876 | A | 6/2000 | Rosenberg et al. | 6,520,908 B1 | 2/2003 | Ikeda et al. |
| 6,080,104 | A | 6/2000 | Ozawa et al. | 6,524,234 B2 | 2/2003 | Ouchi |
| 6,081,809 | A | 6/2000 | Kumagai | 6,530,882 B1 | 3/2003 | Farkas et al. |
| 6,083,152 | A | 7/2000 | Strong | 6,533,722 B2 | 3/2003 | Nakashima |
| 6,083,170 | A | 7/2000 | Ben-Haim | 6,540,669 B2 | 4/2003 | Abe et al. |
| 6,095,971 | A | 8/2000 | Takahashi | 6,544,194 B1 | 4/2003 | Kortenbach et al. |
| 6,099,465 | A | 8/2000 | Inoue | 6,545,703 B1 | 4/2003 | Takahashi et al. |
| 6,100,874 | A | 8/2000 | Schena et al. | 6,551,239 B2 | 4/2003 | Renner et al. |
| 6,104,382 | A | 8/2000 | Martin et al. | 6,558,317 B2 * | 5/2003 | Takahashi et al. ........... 600/158 |
| 6,120,435 | A | 9/2000 | Eino | 6,561,971 B1 | 5/2003 | Akiba |
| 6,125,337 | A | 9/2000 | Rosenberg et al. | 6,565,507 B1 | 5/2003 | Kamata et al. |
| 6,128,006 | A | 10/2000 | Rosenberg et al. | 6,574,629 B1 | 6/2003 | Cooke, Jr. et al. |
| 6,132,369 | A | 10/2000 | Takahashi | 6,589,162 B2 | 7/2003 | Nakashima et al. |
| 6,134,056 | A | 10/2000 | Nakamuka | 6,595,913 B2 | 7/2003 | Takahashi |
| 6,134,506 | A | 10/2000 | Rosenberg et al. | 6,597,390 B1 | 7/2003 | Higuchi |
| 6,135,946 | A | 10/2000 | Konen et al. | 6,599,239 B2 | 7/2003 | Hayakawa et al. |
| 6,139,508 | A | 10/2000 | Simpson et al. | 6,602,186 B1 | 8/2003 | Sugimoto et al. |
| 6,141,037 | A | 10/2000 | Upton et al. | 6,605,035 B2 | 8/2003 | Ando et al. |
| 6,142,956 | A | 11/2000 | Kortenbach et al. | 6,609,135 B1 | 8/2003 | Omori et al. |
| 6,146,355 | A | 11/2000 | Biggs | 6,611,846 B1 | 8/2003 | Stoodley |
| 6,149,607 | A | 11/2000 | Simpson et al. | 6,614,969 B2 | 9/2003 | Eichelberger et al. |
| 6,152,877 | A | 11/2000 | Masters | 6,616,601 B2 | 9/2003 | Hayakawa |
| 6,154,198 | A | 11/2000 | Rosenberg | 6,623,424 B2 | 9/2003 | Hayakawa et al. |
| 6,154,248 | A | 11/2000 | Ozawa et al. | 6,638,214 B2 | 10/2003 | Akiba |
| 6,155,988 | A | 12/2000 | Peters | 6,638,215 B2 | 10/2003 | Kobayashi |
| 6,181,481 | B1 | 1/2001 | Yamamoto et al. | 6,641,528 B2 | 11/2003 | Torii |

| | | | | | | |
|---|---|---|---|---|---|---|
| 6,651,669 B1 | 11/2003 | Burnside | | 6,898,086 B2 | 5/2005 | Takami et al. |
| 6,656,110 B1 | 12/2003 | Irion et al. | | 6,899,673 B2 | 5/2005 | Ogura et al. |
| 6,656,112 B2 | 12/2003 | Miyanaga | | 6,899,674 B2 | 5/2005 | Viebach et al. |
| 6,659,940 B2 | 12/2003 | Adler | | 6,899,705 B2 | 5/2005 | Niemeyer |
| 6,663,561 B2 | 12/2003 | Sugimoto et al. | | 6,900,829 B1 | 5/2005 | Ozawa et al. |
| 6,669,629 B2 | 12/2003 | Matsui | | 6,902,527 B1 | 6/2005 | Doguchi et al. |
| 6,673,012 B2 | 1/2004 | Fujii et al. | | 6,902,529 B2 | 6/2005 | Onishi et al. |
| 6,677,984 B2 | 1/2004 | Kobayashi et al. | | 6,903,761 B1 | 6/2005 | Abe et al. |
| 6,678,397 B1 | 1/2004 | Omori et al. | | 6,903,883 B2 | 6/2005 | Amanai |
| 6,682,479 B1 | 1/2004 | Takahashi et al. | | 6,905,057 B2 | 6/2005 | Swayze et al. |
| 6,685,631 B2 | 2/2004 | Minami | | 6,905,462 B1 | 6/2005 | Homma |
| 6,686,949 B2 | 2/2004 | Kobayashi et al. | | 6,908,427 B2 | 6/2005 | Fleener et al. |
| 6,690,409 B1 | 2/2004 | Takahashi | | 6,908,429 B2 | 6/2005 | Heimberger et al. |
| 6,690,963 B2 | 2/2004 | Ben-Haim et al. | | 6,911,916 B1 | 6/2005 | Wang et al. |
| 6,692,431 B2 | 2/2004 | Kazakevich | | 6,916,286 B2 | 7/2005 | Kazakevich |
| 6,697,101 B1 | 2/2004 | Takahashi et al. | | 6,923,818 B2 | 8/2005 | Muramatsu et al. |
| 6,699,181 B2 | 3/2004 | Wako | | 6,928,490 B1 | 8/2005 | Bucholz et al. |
| 6,702,737 B2 | 3/2004 | Hinto et al. | | 6,930,706 B2 | 8/2005 | Kobayashi et al. |
| 6,711,426 B2 | 3/2004 | Benaron et al. | | 6,932,761 B2 | 8/2005 | Maeda et al. |
| 6,715,068 B1 | 3/2004 | Abe | | 6,934,093 B2 | 8/2005 | Kislev et al. |
| 6,716,162 B2 | 4/2004 | Hakamata | | 6,934,575 B2 | 8/2005 | Ferre et al. |
| 6,728,599 B2 | 4/2004 | Wang et al. | | 6,943,663 B2 | 9/2005 | Wang et al. |
| 6,730,018 B2 | 5/2004 | Takase | | 6,943,821 B2 | 9/2005 | Abe et al. |
| 6,736,773 B2 | 5/2004 | Wendlandt et al. | | 6,943,822 B2 | 9/2005 | Iida et al. |
| 6,743,240 B2 | 6/2004 | Smith et al. | | 6,943,946 B2 | 9/2005 | Fiete |
| 6,749,559 B1 | 6/2004 | Krass et al. | | 6,943,959 B2 | 9/2005 | Homma |
| 6,749,560 B1 | 6/2004 | Konstorum et al. | | 6,943,966 B2 | 9/2005 | Konno |
| 6,749,561 B2 | 6/2004 | Kazakevich | | 6,944,031 B2 | 9/2005 | Takami et al. |
| 6,753,905 B1 | 6/2004 | Okada et al. | | 6,949,068 B2 | 9/2005 | Taniguchi et al. |
| 6,758,806 B2 | 7/2004 | Kamrava et al. | | 6,950,248 B2 | 9/2005 | Rudischhauser et al. |
| 6,758,807 B2 | 7/2004 | Minami | | 6,950,691 B2 | 9/2005 | Uchikubo |
| 6,758,842 B2 | 7/2004 | Irion et al. | | 6,954,311 B2 | 10/2005 | Amanai |
| 6,774,947 B2 | 8/2004 | Muto | | 6,955,671 B2 | 10/2005 | Uchikubo |
| 6,778,208 B2 | 8/2004 | Takeshige et al. | | 6,956,703 B2 | 10/2005 | Saito |
| 6,780,151 B2 | 8/2004 | Grabover et al. | | 6,961,187 B2 | 11/2005 | Amanai |
| 6,785,410 B2 | 8/2004 | Vining et al. | | 6,962,564 B2 | 11/2005 | Hickle |
| 6,785,414 B1 | 8/2004 | McStravick et al. | | 6,963,175 B2 | 11/2005 | Archenhold et al. |
| 6,785,593 B2 | 8/2004 | Wang et al. | | 6,964,662 B2 | 11/2005 | Kidooka et al. |
| 6,796,938 B2 | 9/2004 | Sendai | | 6,967,673 B2 | 11/2005 | Ozawa et al. |
| 6,796,939 B1 | 9/2004 | Hirata et al. | | 6,974,466 B2 | 12/2005 | Ahmed et al. |
| 6,798,533 B2 | 9/2004 | Tipirneni | | 6,975,968 B2 | 12/2005 | Nakamitsu et al. |
| 6,800,056 B2 | 10/2004 | Tartaglia et al. | | 6,976,954 B2 | 12/2005 | Takahashi |
| 6,800,057 B2 | 10/2004 | Tsujita et al. | | 6,977,053 B2 | 12/2005 | Mukasa et al. |
| 6,808,491 B2 | 10/2004 | Kortenbach et al. | | 6,977,670 B2 | 12/2005 | Takahashi et al. |
| 6,824,539 B2 | 11/2004 | Novak | | 6,980,227 B2 | 12/2005 | Iida et al. |
| 6,824,548 B2 | 11/2004 | Smith et al. | | 6,980,921 B2 | 12/2005 | Anderson et al. |
| 6,829,003 B2 | 12/2004 | Takami | | 6,981,945 B1 | 1/2006 | Sarvazyan et al. |
| 6,830,545 B2 | 12/2004 | Bendall | | 6,982,740 B2 | 1/2006 | Adair et al. |
| 6,832,990 B2 | 12/2004 | Kortenbach et al. | | 6,984,206 B2 | 1/2006 | Kumei et al. |
| 6,840,932 B2 | 1/2005 | Lang et al. | | 6,985,183 B2 | 1/2006 | Jan et al. |
| 6,842,196 B1 | 1/2005 | Swift et al. | | 6,986,686 B2 | 1/2006 | Shibata et al. |
| 6,846,286 B2 | 1/2005 | Suzuki et al. | | 6,994,668 B2 | 2/2006 | Miyano |
| 6,847,933 B1 | 1/2005 | Hastings | | 6,994,704 B2 | 2/2006 | Qin et al. |
| 6,849,043 B2 | 2/2005 | Kondo | | 7,001,330 B2 | 2/2006 | Kobayashi |
| 6,850,794 B2 | 2/2005 | Shahidi | | 7,008,376 B2 | 3/2006 | Ikeda et al. |
| 6,855,109 B2 | 2/2005 | Obata et al. | | 2001/0039370 A1 | 11/2001 | Takahashi et al. |
| 6,858,004 B1 | 2/2005 | Ozawa et al. | | 2001/0049491 A1 | 12/2001 | Shimada |
| 6,858,014 B2 | 2/2005 | Damarati | | 2002/0017515 A1 | 2/2002 | Obata et al. |
| 6,860,849 B2 | 3/2005 | Matsushita et al. | | 2002/0028984 A1 | 3/2002 | Hayakawa et al. |
| 6,863,650 B1 | 3/2005 | Irion | | 2002/0055669 A1 | 5/2002 | Konno |
| 6,863,661 B2 | 3/2005 | Carrillo et al. | | 2002/0080248 A1 | 6/2002 | Adair et al. |
| 6,868,195 B2 | 3/2005 | Fujita | | 2002/0087048 A1 | 7/2002 | Brock et al. |
| 6,871,086 B2 | 3/2005 | Nevo et al. | | 2002/0087166 A1 | 7/2002 | Brock et al. |
| 6,873,352 B2 | 3/2005 | Mochida et al. | | 2002/0095175 A1 | 7/2002 | Brock et al. |
| 6,876,380 B2 | 4/2005 | Abe et al. | | 2002/0128633 A1 | 9/2002 | Brock et al. |
| 6,879,339 B2 | 4/2005 | Ozawa | | 2002/0193662 A1 | 12/2002 | Belson |
| 6,881,188 B2 * | 4/2005 | Furuya et al. ............ 600/158 | | 2002/0193664 A1 | 12/2002 | Ross et al. |
| 6,882,785 B2 | 4/2005 | Eichelberger et al. | | 2003/0034863 A1 | 2/2003 | Kazakevich |
| 6,887,195 B1 | 5/2005 | Pilvisto | | 2003/0065250 A1 | 4/2003 | Chiel et al. |
| 6,890,294 B2 | 5/2005 | Niwa et al. | | 2003/0069474 A1 | 4/2003 | Couvillon, Jr. |
| 6,892,090 B2 | 5/2005 | Verard et al. | | 2003/0069897 A1 | 4/2003 | Roy et al. |
| 6,892,112 B2 | 5/2005 | Wang et al. | | 2003/0149338 A1 | 8/2003 | Francois et al. |
| 6,895,268 B1 | 5/2005 | Rahn et al. | | 2003/0181905 A1 | 9/2003 | Long |

| | | | | | | |
|---|---|---|---|---|---|---|
| 2003/0216617 A1* | 11/2003 | Hirakui et al. ............... 600/159 | | 2005/0267417 A1 | 12/2005 | Secrest et al. |
| 2004/0049097 A1 | 3/2004 | Miyake | | 2005/0271340 A1 | 12/2005 | Weisburg et al. |
| 2004/0054258 A1 | 3/2004 | Maeda et al. | | 2005/0272978 A1 | 12/2005 | Brunnen et al. |
| 2004/0073083 A1 | 4/2004 | Ikeda et al. | | 2005/0273085 A1 | 12/2005 | Hinmane et al. |
| 2004/0073084 A1 | 4/2004 | Meada et al. | | 2005/0288545 A1 | 12/2005 | Matsumoto et al. |
| 2004/0073085 A1 | 4/2004 | Ikeda et al. | | 2005/0288553 A1 | 12/2005 | Sugimoto |
| 2004/0143159 A1 | 7/2004 | Wendlandt | | 2006/0015008 A1 | 1/2006 | Kennedy |

FOREIGN PATENT DOCUMENTS

| | | |
|---|---|---|
| 2004/0147809 A1 | 7/2004 | Kazakevich |
| 2004/0167379 A1 | 8/2004 | Akiba |
| 2004/0204671 A1 | 10/2004 | Stubbs et al. |
| 2004/0220452 A1* | 11/2004 | Shalman ..................... 600/157 |
| 2004/0249247 A1 | 12/2004 | Iddan |
| 2004/0257608 A1 | 12/2004 | Tipirneni |
| 2005/0192476 A1 | 9/2005 | Homan et al. |
| 2005/0197861 A1 | 9/2005 | Omori et al. |
| 2005/0200698 A1 | 9/2005 | Amling et al. |
| 2005/0203341 A1 | 9/2005 | Welker et al. |
| 2005/0203418 A1 | 9/2005 | Yamada et al. |
| 2005/0205958 A1 | 9/2005 | Taniguchi et al. |
| 2005/0207645 A1 | 9/2005 | Nishimura et al. |
| 2005/0209509 A1 | 9/2005 | Belson |
| 2005/0225872 A1 | 10/2005 | Uzawa et al. |
| 2005/0226508 A1 | 10/2005 | Gotohda |
| 2005/0228221 A1 | 10/2005 | Hirakawa |
| 2005/0228222 A1 | 10/2005 | Furumi |
| 2005/0228227 A1 | 10/2005 | Weber |
| 2005/0228697 A1 | 10/2005 | Funahashi |
| 2005/0231591 A1 | 10/2005 | Abe |
| 2005/0234507 A1 | 10/2005 | Geske et al. |
| 2005/0243169 A1 | 11/2005 | Ono et al. |
| 2005/0247081 A1 | 11/2005 | Sakata et al. |
| 2005/0250983 A1 | 11/2005 | Tremaglio et al. |
| 2005/0251112 A1 | 11/2005 | Danitz et al. |
| 2005/0251998 A1 | 11/2005 | Bar-Or et al. |
| 2005/0253044 A1 | 11/2005 | Kuriyama |
| 2005/0256370 A1 | 11/2005 | Fujita |
| 2005/0256373 A1 | 11/2005 | Bar-Or et al. |
| 2005/0256377 A1 | 11/2005 | Deppmeier et al. |
| 2005/0256424 A1 | 11/2005 | Zimmon |
| 2005/0264687 A1 | 12/2005 | Murayama |

| | | |
|---|---|---|
| EP | 0 075 153 B1 | 3/1983 |
| EP | 0 278 217 A1 | 8/1988 |
| EP | 0 437 229 A1 | 7/1991 |
| EP | 0 689 851 A1 | 1/1996 |
| EP | 0 728 487 B1 | 8/1996 |
| EP | 1 300 883 A2 | 4/2003 |
| JP | 58-78635 A | 5/1983 |
| JP | 05-31071 A | 2/1993 |
| JP | 05-091972 A | 4/1993 |
| JP | 06-105800 | 4/1994 |
| JP | 06-254048 A | 9/1994 |
| JP | 07-8441 A | 1/1995 |
| JP | 10-113330 A | 5/1998 |
| JP | 10-286221 A | 10/1998 |
| JP | 11-216113 A | 8/1999 |
| JP | 2001 128933 A | 5/2001 |
| JP | 3219521 B2 | 8/2001 |
| JP | 2002 078675 A | 3/2002 |
| JP | 2002-102152 A | 4/2002 |
| JP | 2002-177197 A | 6/2002 |
| JP | 2002-185873 A | 6/2002 |
| JP | 2002-253481 A | 9/2002 |
| JP | 3372273 B2 | 11/2002 |
| JP | 2003-75113 A | 3/2003 |
| JP | 2002 007134 A | 7/2003 |
| JP | 3482238 B2 | 10/2003 |
| WO | WO 93/13704 A1 | 7/1993 |
| WO | WO 2004/016310 A2 | 2/2004 |
| WO | WO 2005/023082 A2 | 3/2005 |

* cited by examiner

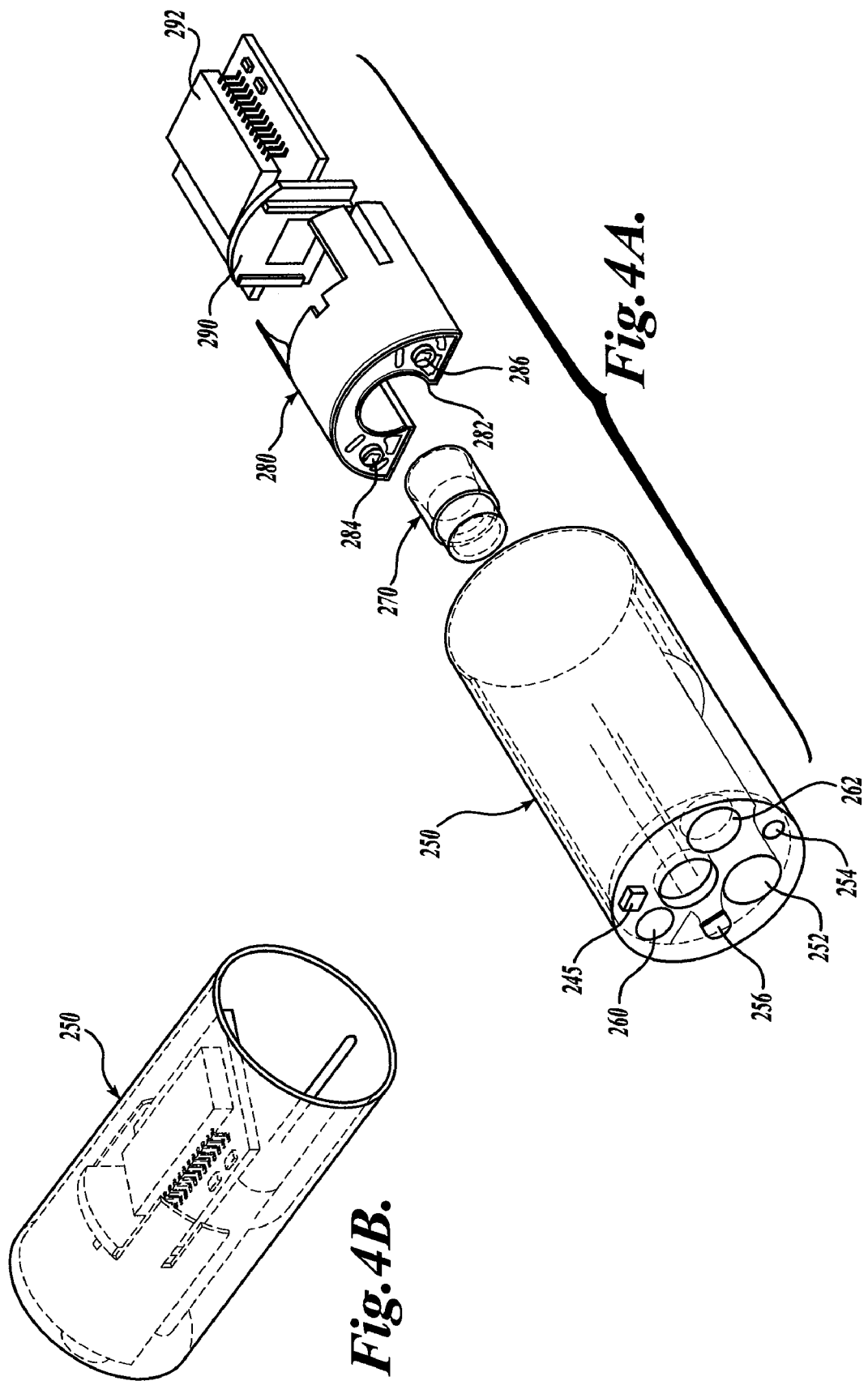

AUTOMATED CONTROL OF IRRIGATION AND ASPIRATION IN A SINGLE-USE ENDOSCOPE

FIELD OF THE INVENTION

The present invention relates to an endoscope system. In particular, it relates to an integrated and automated irrigation and aspiration system for use in an endoscope system.

BACKGROUND OF THE INVENTION

Endoscopes have been used for many years in the medical field to look within a selected region of a patient's body or to perform surgical, therapeutic, diagnostic, or other medical procedures under direct visualization. A conventional endoscope generally contains several components including illuminating means such as light-emitting diodes or fiber optic light guides connected to a proximal source of light, an imaging means such as a miniature video camera or a fiber optic image guide, and a working channel. These components are positioned within an endoscope sheathing tube. Flexible or steerable endoscopes also incorporate an elongated flexible shaft and an articulating distal tip to facilitate navigation through the internal curvature of a body cavity or channel.

Colonoscopy is a medical procedure in which a flexible endoscope, or colonoscope, is inserted into a patient's colon for diagnostic examination and/or surgical treatment of the colon. A standard colonoscope is typically 135-185 cm in length and 12-13 mm in diameter. Colonoscopes generally include a fiber optic imaging bundle, illumination fibers, one or two instrument channels that may also be used for insufflation or irrigation, and a suction channel that extends the length of the colonoscope to facilitate removal of occlusions such as mucus, plaque, fecal matter, or other material that can obstruct the physician's view or interfere with the endoscopic procedure. The colonoscope is inserted via the patient's anus and is advanced through the colon, allowing direct visual examination of the colon, the ileocecal valve, and portions of the terminal ileum. Approximately six million colonoscopies are performed each year.

In order to examine a patient's anatomy during a colonoscopy, it is essential to have a clear field of view. Currently, about 20% of colon polyps are undetected due to low visibility, which can arise from inadequate lens cleaning. Poor colon preparation is also a cause of reduced visibility in the colon. Presently, about 10% of all patients are non-compliant with preparatory procedures and approximately 4% of all patients are unable to complete the exam due to an excess of stool in the colon. The remaining 6% of all cases are considered marginal, and the colonoscopy may still be performed if the colon is evacuated as a part of the procedure. Conventionally, the colons of marginal cases are cleared by repeatedly administering several small (60 cc) fluid flushes through an endoscope's working channel by means of an ancillary apparatus that employs a low-volume wash and suction. The waste is then removed through the suction channel in the endoscope. However, this tedious and inefficient process is limited by the amount of stool that can be removed with each flush. The process also causes a loss of productivity due to the added time required to evacuate the colon. Therefore, there is a need for a system and method of efficiently cleaning poorly prepared colons.

One example of a colon irrigation method for colonoscopy is described in U.S. Pat. No. 5,279,542, entitled "Colon Irrigation Method." The '542 patent describes an irrigation instrument for use in evacuating the colon prior to endoscopic surgery. The instrument consists of an elongate tube with a plurality of longitudinally and circumferentially spaced apertures along its entire length. A pressurized source of irrigation fluid is connected to the tube for feeding fluid through the channel and out through the apertures with an essentially uniform radial distribution. The tube is thin enough to fit down the biopsy channel of an endoscope. The invention essentially provides an improved method for providing irrigating fluid to a distal end of an endoscope or to a surgical site.

Although the apparatus and method of the colon irrigation method described in the '542 patent provides a means of irrigation for colonoscopy and other endoscopic procedures, the device is an accessory to standard endoscopes that uses the working channel of the endoscope. As such, the apparatus requires labor-intensive assembly on an as-needed basis. Furthermore, it is up to the physician to determine the amount of cleaning that is required and to control the apparatus such that the patient is sufficiently prepped for an examination. This reduces the time that the physician has to perform the actual examination.

Given these problems, there is a need for a system that can automatically prepare poorly prepped patients for an endoscopic examination with minimal physician supervision. In addition, the system should operate based on the patient's individual physical anatomy and detected level of cleanliness so that a desired field of view is created in which an examination is conducted.

SUMMARY OF THE INVENTION

To address the foregoing deficiencies in the prior art, the present invention is an endoscopic system that provides automated irrigation and aspiration of patients undergoing colonoscopy. The endoscopic examination system according to the present invention includes an endoscope with a source of illuminative light and an image sensor to produce images of a patient's colon. An image processor is coupled to receive image signals from the image sensor. The image processor or a computer automatically analyzes the images obtained from the image sensor to determine if irrigation and aspiration is required to provide a clear field of view. If so, the computer operates one or more control valves that supply the insufflation, irrigation, and aspiration to the patient.

In one embodiment, the endoscope may include one or more sensors that sense environmental conditions within the patient's colon such that the amount, rate, or composition of the cleaning solution delivered can be adjusted to the patient's individual anatomy and level of preparation. In one embodiment, the level of insufflation and aspiration are automatically adjusted to provide a desired field of view in the region of the distal tip of the endoscope.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIGS. 4A and 4B illustrate an imaging sensor and heat exchanger positioned at the distal end of the endoscope in accordance with an embodiment of the present invention.

DETAILED DESCRIPTION OF THE PREFERRED EMBODIMENT

As indicated above, the present invention is an endoscopic examination system that provides integrated and automated irrigation and aspiration for prepping poorly prepared patients for examination. The system is integral to the overall endoscope architecture. Further, the physical hardware implementation of the endoscope improves upon previous means of irrigation by the use of an automated mechanism that administers one or more colon irrigation modalities depending on an analysis of the patient's anatomy or level of preparation. Although the present invention is described with respect to its use within the colon, it will be appreciated that the invention can be used in any body cavity that can be expanded and/or prepared for examination or surgery.

Figure 1:
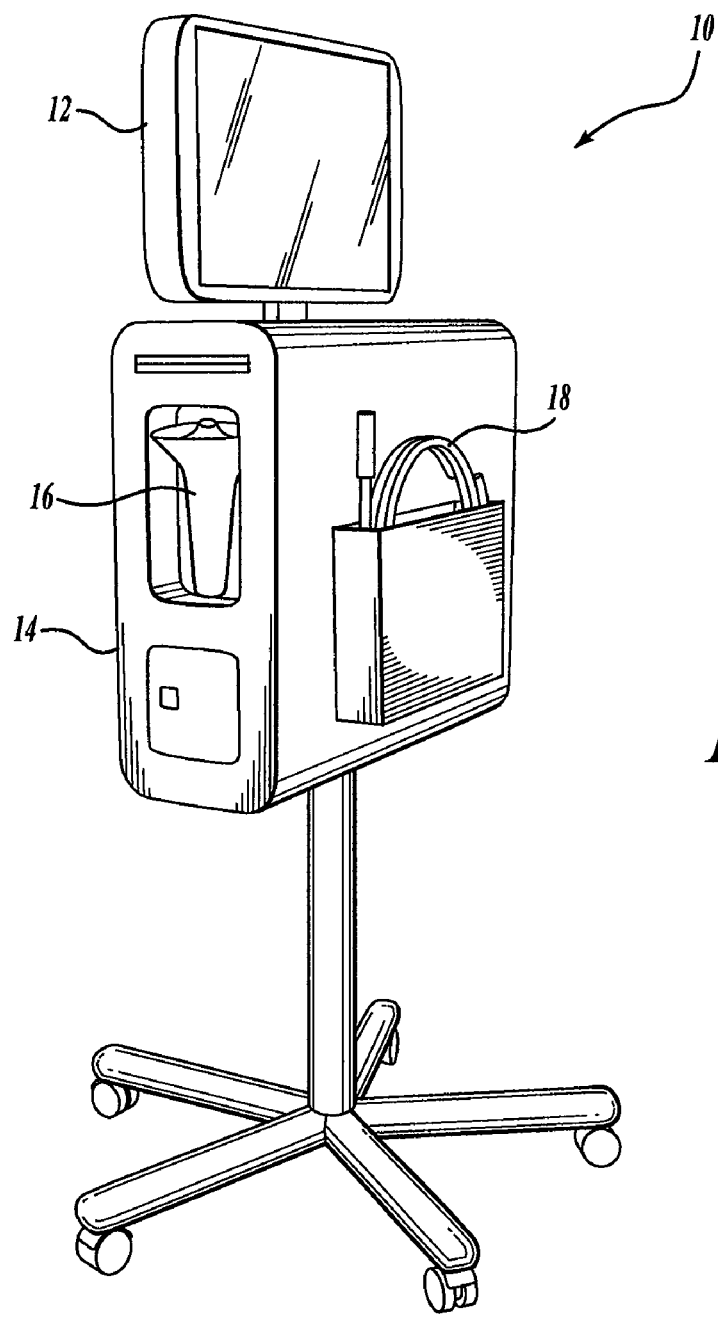
FIG. 1 illustrates a single-use endoscopic imaging system in accordance with one embodiment of the present invention.

FIG. 1 illustrates the major components of an exemplary single-use endoscopic imaging system 10. The components of the system 10 include a display 12, a user input device 16, and a single-use imaging endoscope 18, all of which are functionally connected to a control cabinet 14 that executes application software (not shown) residing therein. Display 12 is any special-purpose or conventional computer display device, such as a computer monitor, that outputs graphical images and/or text to a user. Single-use imaging endoscope 18 is a single-use flexible tube that contains one or more lumens for the purpose of performing endoscopic procedures and facilitating the insertion and extraction of fluids, gases, and/or medical devices into and out of the body. Single-use endoscope 18 further contains a digital imaging system (not shown) comprised of, in one example, an image sensor such as a CMOS imager, optical lenses such as plastic optics, a light source such as a number of LEDs, and an articulating tip that enables steering of the endoscope in a desired direction.

Control cabinet 14 is a special-purpose electronic and electro-mechanical apparatus that processes and manages all system functions, and includes a network-enabled image-processing CPU, a physical connection to the single-use endoscope 18, an optional dock for the user interface 16, and valves that control the delivery of gas/water to the endoscope and a vacuum line that removes the air/gas and debris, etc., from the patient. User input device 16 is a hand-held device, either wired to the control cabinet 14 or wireless, that accepts inputs from a human operator via standard push buttons, joysticks, or other activation devices either singularly or in combination to control the operation of single-use endoscopic imaging system 10.

Operation of single-use endoscopic imaging system 10 is as follows: the system is initiated and operated upon command by means of user input device 16, causing the application software executed by a processor within the control cabinet 14 to activate the appropriate hardware to perform surgical, therapeutic, diagnostic, or other medical procedures and to deliver insufflation and/or suction to the lumen(s) of single-use endoscope 18. Display 12 provides live endoscopic video images and visual feedback of control parameters to the physician or operator so that an examination of the patient can be completed. Upon termination of the examination, the endoscope 18 is disconnected from the control cabinet and disposed of.

Figure 2:
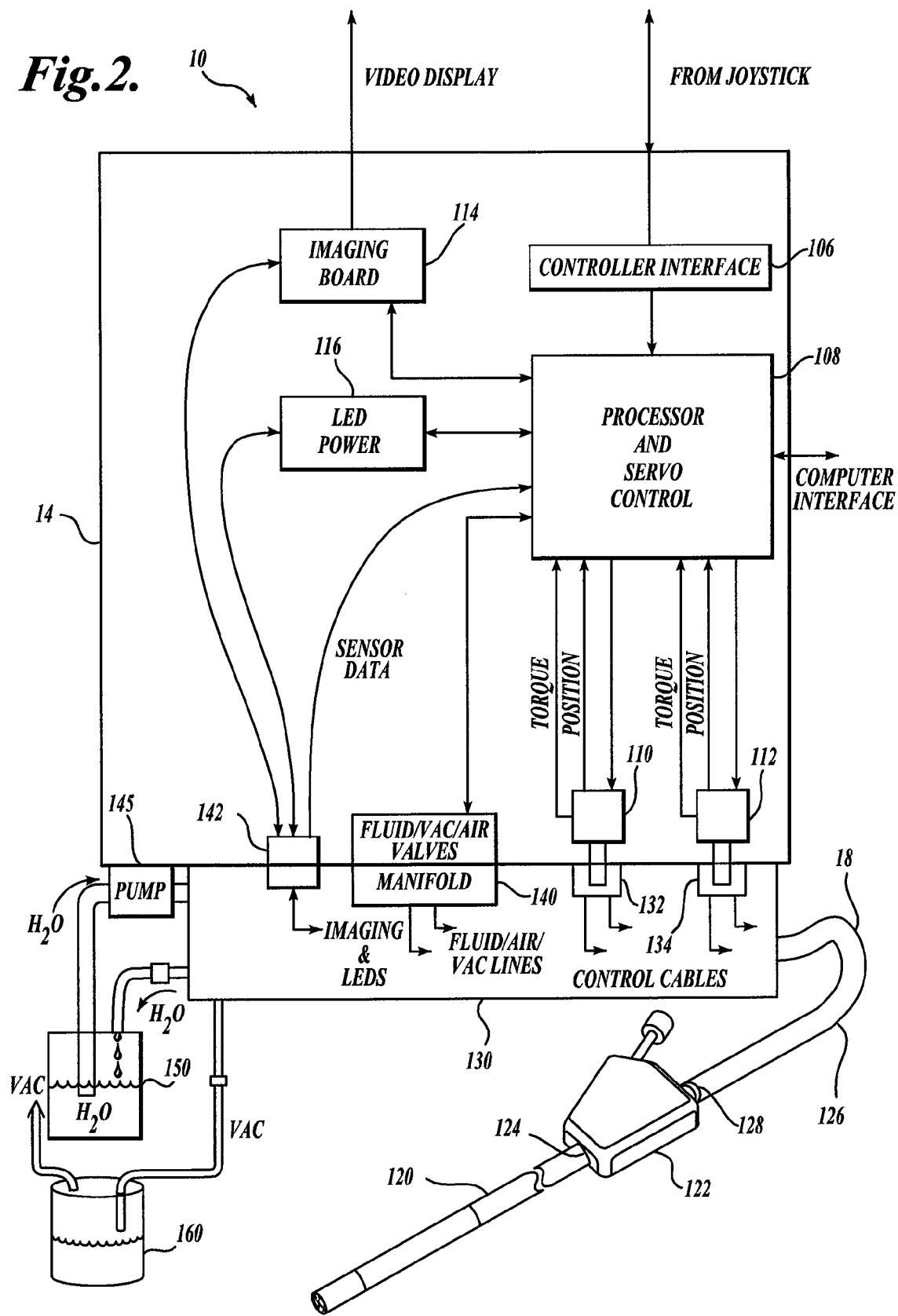
FIG. 2 is a functional block diagram that shows the interrelationship of the major components of a single-use endoscopic imaging system shown in FIG. 1.

FIG. 2 is a functional block diagram of single-use endoscopic imaging system 10 that shows the operational interrelationship of the major hardware and software elements of the system. A complete description of the control cabinet 14 and other components is set forth in U.S. patent application Ser. No. 10/811,781, filed Mar. 29, 2004, and U.S. patent application Ser. No. 7,413,543, entitled VIDEO ENDOSCOPE and herein incorporated by reference. The single-use endoscopic imaging system 10 includes the control cabinet 14 that operates to control the orientation and functions of a single-use imaging endoscope 18. The control cabinet 14 includes a controller interface 106 that receives commands from the user input device 16 such as a joystick, that is used by a physician or their assistant to control the operation of the single-use endoscope 18. Commands from the joystick are supplied to a programmable processor such as a digital signal processor that controls the overall operation of the imaging system and a servo control unit 108. The processor and servo control unit 108 control the operation of a pair of servo motors 110, 112 that in turn drive control cables within the single-use endoscope 18. The orientation of the distal tip is controlled in response to directional signals received from the user input device as well as feedback signals obtained from sensors that measure the position and torque of each of the servo motors 110, 112.

In one embodiment of the invention, the processor and servo control unit 108 implement a position-to-rate control that varies the speed at which the distal tip is moved as a function of the position of the directional switch on the user input device 16. However, other control algorithms such as position-to-position or position-to-force (i.e., acceleration) could also be implemented.

The control cabinet 14 also includes an imaging board 114 that produces images from the signals that are received from the image sensor at the distal end of the single-use endoscope 18. The imaging board 114 deserializes the digital video signals from the CMOS imager sensor and performs the necessary algorithms such as demosaicing, gain control and white balance to produce a quality color image. The gain control of the system is implemented by adjusting the intensity of the illumination (current supplied to a number of LEDs) and adjusting the RGB gains of the CMOS imager. The imaging board 114 also includes isolation circuitry to prevent a patient from becoming shocked in the event of an electrical failure on the imaging board 114 or within the control cabinet 14 as well as circuitry for transmitting control signals to the image sensor and for receiving image signals from the image sensor. In one embodiment of the invention, the imaging board 114 is provided on a standard PC circuit board to allow individual endoscopes to be tested with a personal computer and without the need for an additional control cabinet 14.

In the embodiment shown in FIG. 2, the single-use endoscope 18 has a distal shaft portion 120 that is connected to a breakout box 122 with a swivel connection 124. The breakout box 122 provides access to a working channel in the distal portion of the endoscope. In addition, the proximal portion 126 of the shaft is connected to the breakout box 122 with a second swivel connection 128. The swivel connections 124, 128 allow the distal and proximal ends of the endoscope to rotate with respect to the breakout box 122 and without twisting the breakout box 122 in the hands of the physician or their assistant.

In the embodiment shown, the single-use endoscope 18 is connected to the control cabinet 14 with a connector 130. Within the connector 130 are a pair of spools 132, 134 that are engageable with the driveshafts of the servo motors 110, 112. Each spool 132, 134 drives a pair of control cables that are wound in opposite directions. One pair of control cables drives the distal tip of the endoscope in the up and down direction, while the other pair of control cables drives the distal tip of the endoscope in the left and right direction. In an alternate embodiment, the endoscope may include a manual handle having control knobs that selectively tension or release the control cables to move the distal tip and one or more buttons that activate functions of the endoscope.

The connector 130 also includes a manifold 140 that controls the supply of irrigation fluid, air and vacuum to various tubes or lumens within the endoscope 18. In addition, the connector 130 includes an electrical connector 142 that mates with the corresponding electrical connector on the control cabinet 14. The connector 142 transfers signals to and from the image sensor as well as power to the illumination LEDs and allows connection to a thermal sensor at the distal end of the endoscope. In addition, the connector 142 carries signals from one or more remotely located environmental sensors as will be described below. Water or another irrigation liquid is supplied to the endoscope with a pump 145. The pump 145 is preferably a peristaltic pump that moves the water though a flexible tube that extends into the proximal connector 130. Peristaltic pumps are preferred because the pump components do not need to come into contact with the water or other fluids within the endoscope and it allows the wetted component to be single-use. A water or other irrigation liquid reservoir 150 is connected to the pump 145 and supplies water to cool the illumination LEDs as well as to irrigate the patient. The water supplied to cool the LEDs is returned to the reservoir 150 in a closed loop. Waste water or other debris are removed from the patient with a vacuum line that empties into a collection bottle 160. Control of the vacuum to the collection bottle 160 is provided at the manifold 140 within the proximal connector 130. A gas source provides insufflation by delivering an inert gas such as carbon dioxide, nitrogen, air, etc., to the lumen(s) of single-use endoscope 18 via the manifold 140.

The processor and control unit 108 executes application software, including a GUI software application, a system control software application, and a network software application that reside on a computer readable medium such as a hard disc drive, CD-ROM, DVD, etc., or in a solid state memory. GUI software application is well known to those skilled in the art, and provides the physician or operator with live endoscopic video or still images and, optionally, with visual, audible, or haptic control and feedback on display 12 using user input device 16. System control software application is the central control program of application software that receives input from sensors, such as from the one or more environmental sensors at the distal end of the endoscope as described below, as well as from the input device 16. System control software application provides system control for the functions necessary to operate single-use endoscope system 10. The network software application operates a network connection to allow the endoscopic imaging system 10 to be connected to a local area network and/or the Internet.

As set forth in the Ser. No. 10/811,781 application, the manifold 140 supplies insufflation gas, water and vacuum to one or more lumens of single-use endoscope 18. The manifold is preferably constructed as a series of passages that are formed between sheets of a thermoplastic material. Water, air, and vacuum are applied to inputs of the manifold and selectively delivered to outputs that are in turn connected to lumens within the endoscope 18 by pinch valves on the control cabinet 14 that open or close the passages in the manifold. The passages are preferably formed by rf welding the sheets of thermoplastic into the desired pattern of the passages.

Figure 3:
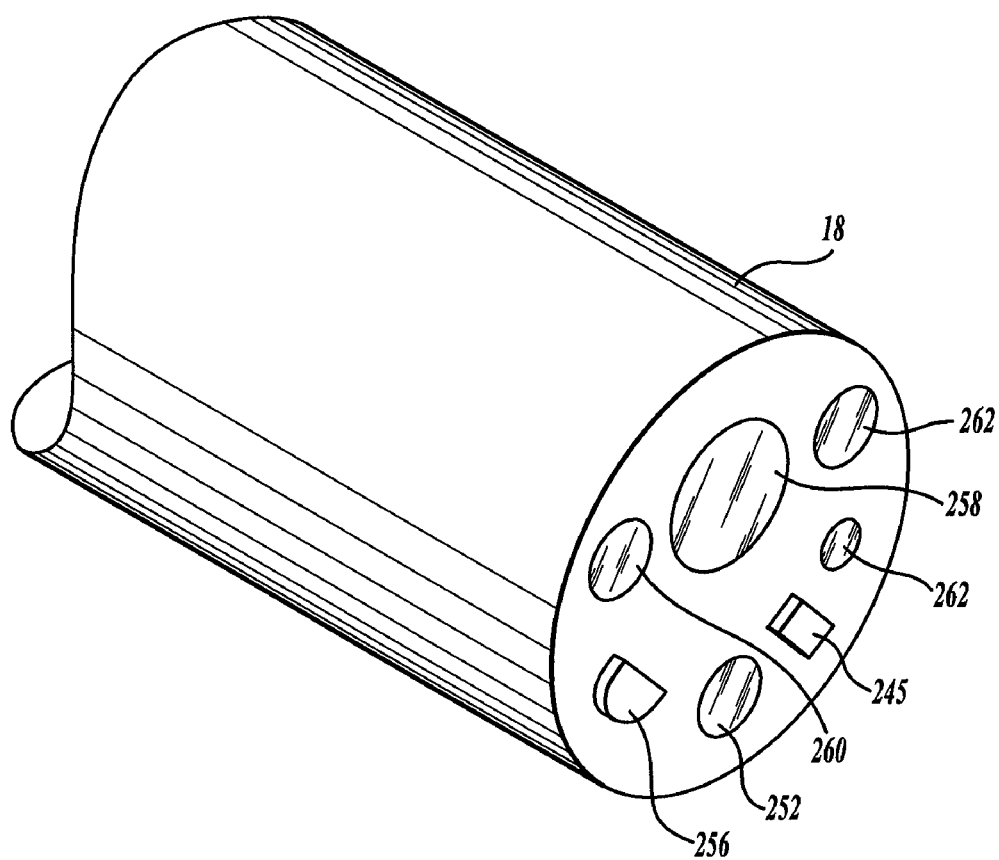
FIG. 3 illustrates a distal end of a single-use imaging endoscope in accordance with an embodiment of the present invention.

In accordance with FIG. 2, the basic process of insufflation and exsufflation using single-use endoscopic imaging system 10 is as follows:

During operation, live endoscopic video images are provided on display 12 by the GUI software application, which processes information from the imaging board 114, and the single-use endoscope 18. Prior to operation, insufflation is initiated upon operator command by means of the user input device 16, or according to a pre-programmed routine. As a result, system control software application activates the manifold 140 by means of the pinch valves on the control cabinet 14. Upon advancing single-use endoscope 18, images are produced by the image sensor at the distal tip of the endoscope and analyzed by the image processor 114 and/or the processor and servo control unit 108 to determine if either irrigation or insufflation is required. If insufflation is required, an insufflation gas is channeled through a lumen of single-use endoscope 18 and into the patient. In one embodiment of the invention, the gas delivery lumen terminates at directional port 256, that directs the insufflation gas and/or irrigation liquid over a lens 270 of the imaging sensor, as shown in FIG. 3. As the distal tip of single-use endoscope 18 is advanced into the colon during the endoscopic procedure, further areas of the colon are insufflated, bringing new examination regions into view.

As shown in FIG. 3, the distal end of the single-use endoscope 18 includes a distal cap 250 having a number of openings on its front face. The openings include an opening to a working channel 252 and an opening 254 for a low pressure lavage lumen, whereby a stream of liquid can be delivered through the endoscope to remove debris or obstructions from the patient. A lens wash and insufflation port includes the integrated directional port or flush cap 256 that directs water across the lens of an image sensor and delivers the insufflation gas to expand the lumen in which the endoscope is inserted. Offset from the longitudinal axis of the endoscope is a lens port 258 that is surrounded by a pair of windows or lenses 260 and 262 that cover the illumination sources. One or more environmental sensors 245 are also disposed on or adjacent the front face of the distal cap 250 to detect environmental conditions within the body cavity of the patient. Signals from the one or more environmental sensors are transmitted back to the processor and servo control unit 108 through the electrical connector 142. Suitable environmental sensors 245 include, but are not limited to, pressure, temperature, pH sensors to measure conditions in the patient adjacent the distal tip. In addition, sensors such as laser distance sensor or ultrasonic probes can be used to measure the size of the area or thickness of the colon wall surrounding the endoscope.

As best shown in FIG. 4A, the imaging assembly at the distal end of the endoscope also includes a heat exchanger 280. The heat exchanger 280 comprises a semi-circular section having a concave recess 282 into which a cylindrical lens assembly 270 is fitted. The concave recess 282 holds the position of the lens assembly 270 in directions perpendicular to the longitudinal axis of endoscope, thereby only permitting the lens assembly 270 to move along the longitudinal axis of the endoscope. Once the lens assembly is positioned such that it is focused on an image sensor 290 that is secured to a rear surface of the heat exchanger 280, the lens assembly is fixed in the heat exchanger with an adhesive. A pair of LEDs 282, 284 are bonded to a circuit board that is affixed in the heat exchanger such that a channel is formed behind the circuit board for the passage of a fluid or gas to cool the LEDs. A circuit board or flex circuit 292 containing circuitry to transmit and receive signals to and from the control cabinet is secured behind the image sensor 290 and to the rear surface of the heat exchanger 280. With the lens assembly 270, the LEDs 280, 282, the image sensor 290, and associated circuitry 292 secured in the heat exchanger 280, the heat exchanger assembly can be fitted within the distal cap 250 to complete the imaging assembly.

As discussed, the images obtained from the image sensor are analyzed by an image analysis program to determine when cleaning of the imaging system or the colon itself is desired. In addition, measurements of the colon cavity obtained from the one or more environmental sensors may be combined with image information as analyzed by the image analysis program to control the supply of irrigation and aspiration when a cleaning cycle is required.

The basic process of irrigation and aspiration for the purpose of prepping a poorly prepared patient during a colonoscopy procedure using the endoscopic imaging system 100 is as follows.

The GUI software application displays the live video or still images produced by the imaging board 114 on the display 110. In addition, an image analysis program that is executed by a processor on the imaging board 114 or the processor and servo control unit 108 analyzes the image signals to determine if it is necessary to employ a wash routine in the patient or to clean the lens of the endo scope 18. If the image analysis program determines that a lens cleaning or wash routine should be initiated, the control software application activates one or more valves controlling the manifold to deliver an irrigation liquid and vacuum aspiration to the endoscope. The modality of the washing routine supplied can be determined based on an analysis of the images produced as well as volumetric, environmental or other measurements obtained by the one or more environmental sensors 245 at the distal end of the endoscope.

To determine if the field of view of the single-use endoscope 18 is clear or obstructed, the image analysis program analyzes images of the patient's body for the presence of obstructing matter within the area of view or on the surface of imaging optics. For example, the image analysis program determines if the position of an obstruction changes with a change in probe position. If an obstruction remains in the same place within an image despite moving the endoscope, then the system control software initiates a blast of cleaning solution over the surface of the imaging lens. However, if the image appears to indicate that the patient has not been properly prepped, then the system control software proceeds to initiate one or more cleaning or washing routines.

In one embodiment of the invention, the presence of obstructing material in the field of view is detected by the image analysis program on the basis of the color or spectral reflectance of the tissue being observed. Healthy colon tissue is typically characterized by white or pinkish tissue. Therefore, the image analysis program searches an image to determine the number of pixels in the image that display the desired tissue color. If the image contains too many dark or other colored pixels, the presence of obstructing material is presumed. Of course, it will be appreciated that the color of healthy, clean tissue can vary from patient to patient. Therefore, the physician may be prompted to direct the probe at a known portion of healthy, clean tissue to calibrate the image analysis program prior to beginning the colonoscopy.

In performing the washing routine, the system control software may take into consideration measurements obtained from the one or more environmental sensors 245 included in the single-use endoscope 18. For example, measurements of the size of the colon cavity, thickness of the colon wall, pressure within the colon, or other factors such as temperature, pH, etc. can be obtained from the one or more environmental sensors 245 and used to adjust the volume or rate of delivery and/or aspiration of liquid supplied or the composition of the washing liquid can be adjusted based on the measurements obtained. Similarly, the environmental sensor 245 positioned along the length of the endoscope can measure the depth of insertion of the distal tip of the endoscope.

With the endoscopic imaging system 10, any obstructions that interfere with the endoscopic procedure are automatically detected. Washing or lens cleaning routines are initiated upon command by the system control software or may be initiated by an operator command received via user interface 16. Wash routines may include, for example, a continuous spray, a pulsating jet, and a large bolus wash. Sequential mixtures of fluids or gases can be augmented with aeration and/or additives. Additives are added into the irrigant solution, either singularly or in combination, upon operator command using user interface 16 or as directed by preprogrammed wash routines or based on an analysis of signals produced from the image sensor and/or the one or more environmental sensors 245. New wash routines may be downloaded through network connection by means of network software application. Alternatively, a user may also manually define new irrigant mixes and/or wash routines by recording a series of operator commands on user interface 16.

After irrigation, the resulting maceration is aspirated under control of the system control software application, which activates the manifold 140. The manifold 140 applies vacuum through a working or aspiration channel of the single-use endoscope 18. At any time, the physician or their assistant may manually interrupt the wash routine or aspiration.

The endoscopic imaging system of the present invention also determines if the body cavity is properly inflated. Such a determination is made by measuring the pressure and/or analyzing images obtained from the image sensor. If the body cavity is not properly inflated, insufflation gas is delivered to the patient in a manner that is adjusted for environmental conditions in the patient. As with the washing mode, the insufflation gas can be delivered in accordance with the detected pressure in the body cavity, the size of the cavity, or until the image signals produced by the image sensor indicate that the colon is inflated to produce a desired field of view. Furthermore, the insufflation gas can be adjusted in accordance with the sensed thickness of the colon wall or other parameters that assure that insufflation gas is not delivered too quickly so as to cause discomfort or potential injury to the patient. By automatically controlling the insufflation of the colon at the region of the distal tip a desired field of view is provided and inadvertent collapse of the colon is prevented. Furthermore, the physician can concentrate on performing the procedure without having to manually control insufflation.

As will be appreciated, the automated irrigation and aspiration features of the present invention reduce the need for the physician to actively control the preparation of poorly prepared patients for examination. Because obstructions and poor fields of view are automatically detected and cleared, the physician can concentrate on performing the required procedure. Furthermore, the evacuation wash routines may be tailored to a patient's individual condition as detected by the image analysis program and one or more sensors 122.

While the preferred embodiment of the invention has been illustrated and described, it will be appreciated that various changes can be made therein without departing from the scope of the invention. For example, although the present invention is described with respect to single use, disposable endoscopes, it will be appreciated that the present invention is also applicable to non-disposable, reusable endoscopes as well. It is therefore intended that the scope of the invention be determined from the following claims and equivalents thereof.

The embodiments of the invention in which an exclusive property or privilege is claimed are defined as follows:

1. An endoscopic imaging system, comprising:
   a control unit that is connectable to an endoscope that has an image sensor to be inserted within a patient;
   a processor configured to analyze images produced by the image sensor of an endoscope;
   a source of irrigation and aspiration connected to the control unit and configured to be selectively controlled by the processor to deliver an irrigant through the endoscope and to aspirate the irrigant from the endoscope when the processor detects a blockage in a field of view of the image sensor; and
   a computer-readable storage medium having computer-executable instructions stored thereon that, when executed by the processor, cause the processor to perform a method of image analysis and source of irrigation and aspiration control by:
      determining if the field of view of the endoscope is obstructed based on at least an image signal obtained from the image sensor; and
      controlling the source of irrigation and aspiration to deliver an irrigant through the endoscope and to aspirate the irrigant from the endoscope to remove the obstruction.

2. The endoscopic imaging system of claim 1, further comprising one or more environmental sensors disposed within the endoscope, and wherein the method further comprises:
   receiving signals from the one or more environmental sensors; and
   adjusting the operation of the source of irrigation and aspiration as a function of the signals received from the one or more environmental sensors.

3. The system of claim 2, wherein the one or more environmental sensors include a sensor for measuring the size of a cavity in which the endoscope is placed, and wherein the processor controls the source of irrigation and aspiration as a function of the cavity size.

4. The system of claim 2, wherein the one or more environmental sensors include a pressure sensor, and wherein the processor controls the source of irrigation and aspiration as a function of the sensed pressure.

5. The system of claim 2, wherein the one or more environmental sensors include a sensor that detects a thickness of a colon wall and wherein the processor controls the source of irrigation and aspiration as a function of the colon wall thickness.

6. The system of claim 1, wherein the computer-executable instructions that cause the processor to determine if the field of view of the endoscope is obstructed based on at least an image signal obtained from the image sensor further include instructions for:
   analyzing the image for a number of pixels having a color not representative of clean colon tissue; and
   indicating a blockage based on the number of such pixels.

7. The system of claim 6, wherein the computer-executable instructions that cause the processor to determine if the field of view of the endoscope is obstructed based on at least an image signal obtained from the image sensor further include instructions for obtaining an image of the patient's clean healthy colon tissue to calibrate the method of image analysis.

8. A method performed by a computer processor for automatically initiating a wash cycle to a patient undergoing a colonoscopy, comprising:
   receiving a first image of colon tissue from an image sensor at a distal end of an endoscope;
   receiving a second image of colon tissue from the image sensor;
   comparing a color of a portion of the second image to a color of a portion of the first image to detect the presence of an obstruction in the field of view of the image sensor; and
   if the color of the portion of the second image is not representative of the color of the portion of the first image, automatically initiating the wash cycle to remove the obstruction.

9. The method of claim 8, further comprising obtaining a measurement from an environmental sensor within the patient and controlling the wash cycle as a function of the measurement obtained.

10. The method of claim 9, wherein the measurement is obtained by measuring the size of the colon adjacent the distal end of the endoscope.

11. The method of claim 9, wherein the measurement is obtained by measuring the pressure adjacent the distal end of the endoscope.

12. The method of claim 9, wherein the measurement is obtained by measuring the thickness of the colon wall adjacent the distal end of the endoscope.

13. The method of claim 9, wherein the measurement is obtained by measuring the depth of insertion of the endoscope adjacent the distal end of the endoscope.

* * * * *